(12) United States Patent
Sauer et al.

(10) Patent No.: US 12,426,875 B2
(45) Date of Patent: Sep. 30, 2025

(54) SPINAL ANNULOTOMY CLOSURE SEWING DEVICE

(71) Applicant: LSI Solutions, Inc., Victor, NY (US)

(72) Inventors: Jude S. Sauer, Pittsford, NY (US); John F. Hammond, Canandaigua, NY (US)

(73) Assignee: LSI Solutions, Inc., Victor, NY (US)

( * ) Notice: Subject to any disclaimer, the term of this patent is extended or adjusted under 35 U.S.C. 154(b) by 231 days.

(21) Appl. No.: 18/115,434

(22) Filed: Feb. 28, 2023

(65) Prior Publication Data

US 2023/0270434 A1    Aug. 31, 2023

Related U.S. Application Data

(60) Provisional application No. 63/314,889, filed on Feb. 28, 2022.

(51) Int. Cl.
*A61B 17/04* (2006.01)
*A61B 17/06* (2006.01)

(52) U.S. Cl.
CPC .......... *A61B 17/0483* (2013.01); *A61B 17/06* (2013.01)

(58) Field of Classification Search
CPC ............... A61B 17/0483; A61B 17/06; A61B 17/06061; A61B 17/06066; A61B 2017/06052

See application file for complete search history.

(56) References Cited

U.S. PATENT DOCUMENTS

| | | |
|---|---|---|
| 5,562,686 A | 10/1996 | Sauer et al. |
| 5,643,289 A | 7/1997 | Sauer et al. |
| 5,669,917 A | 9/1997 | Sauer et al. |
| 6,533,796 B1 | 3/2003 | Sauer et al. |
| 6,641,592 B1 | 11/2003 | Sauer et al. |
| 7,833,237 B2 | 11/2010 | Sauer |
| 10,603,027 B2 | 3/2020 | Sauer |
| 10,799,227 B2 | 10/2020 | Sauer |
| 10,939,904 B2 | 3/2021 | Sauer et al. |
| 11,116,496 B2 | 9/2021 | Sauer |
| 11,357,500 B2 | 6/2022 | Sauer |
| 2017/0360430 A1* | 12/2017 | Sauer ................. A61B 17/0206 |
| 2020/0078012 A1* | 3/2020 | Sauer ................. A61B 17/0469 |

* cited by examiner

Primary Examiner — Katherine M Shi
Assistant Examiner — Mohammed S Adam
(74) Attorney, Agent, or Firm — Michael E. Coyne

(57) ABSTRACT

A device includes a selection lever pivotably coupled to a housing, a shaft coupled to the housing, and a distal end assembly coupled to the shaft. When the selection lever is in a first position and an actuation lever is pivoted from a first position to a second position, a tip of the first needle extends from a first position across a first tissue bite area to a second position in which the tip is disposed within a first ferrule recess of a receiver portion of the distal end assembly. When the selection lever is in a second position and the actuation lever is pivoted from the first position to the second position, a tip of the second needle extends from a first position across a second tissue bite area to a second position in which the tip is disposed within a second ferrule recess of the receiver portion.

3 Claims, 12 Drawing Sheets

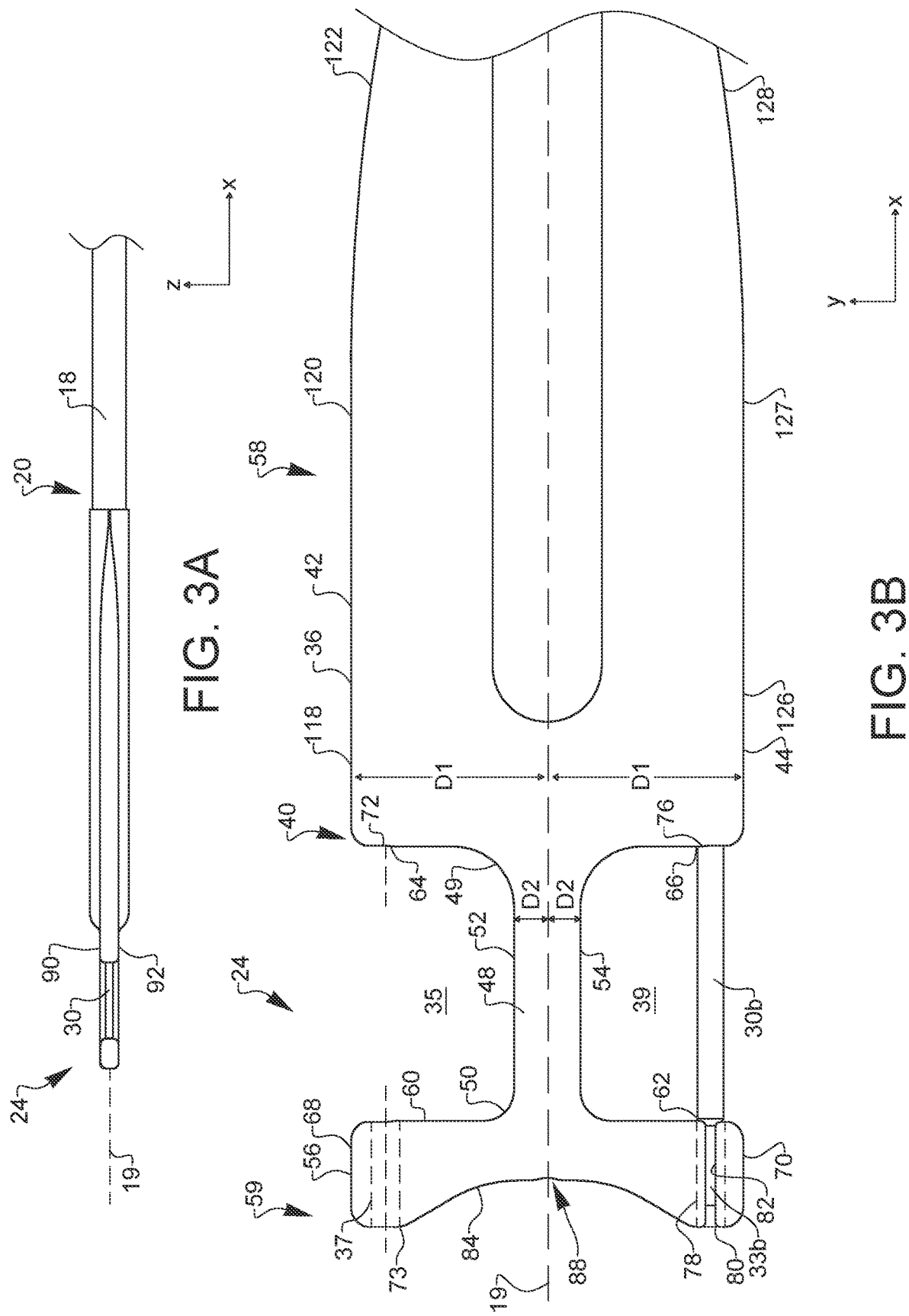

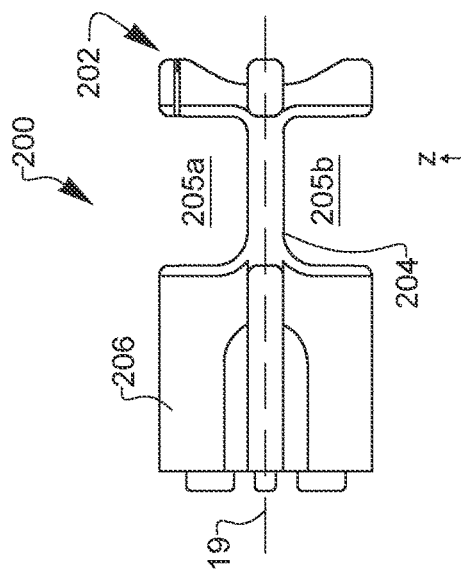
FIG. 4A
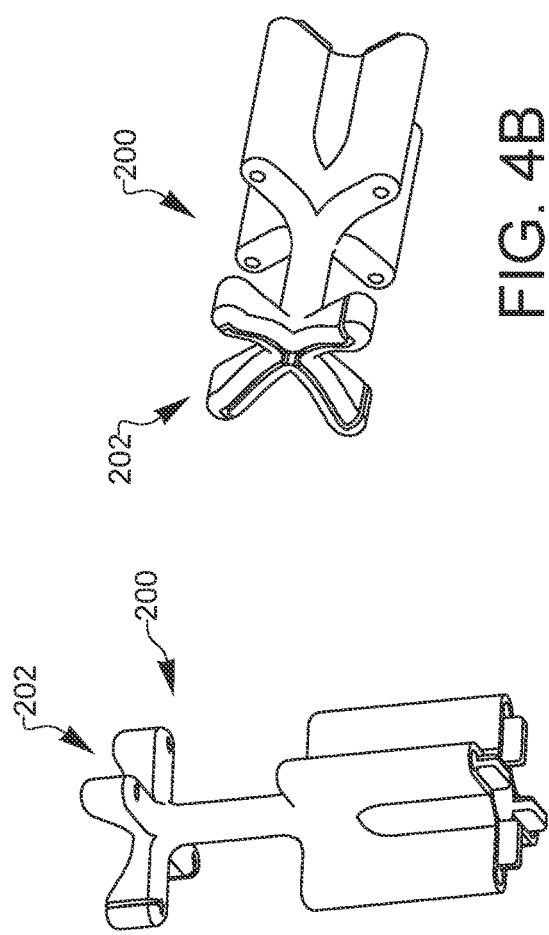
FIG. 4B
FIG. 4C
FIG. 4D
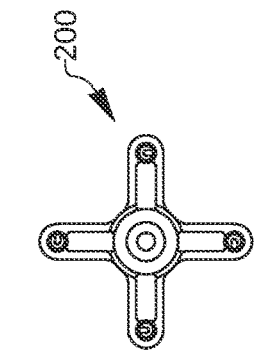
FIG. 4E
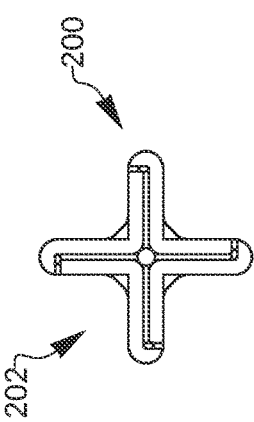
FIG. 4F

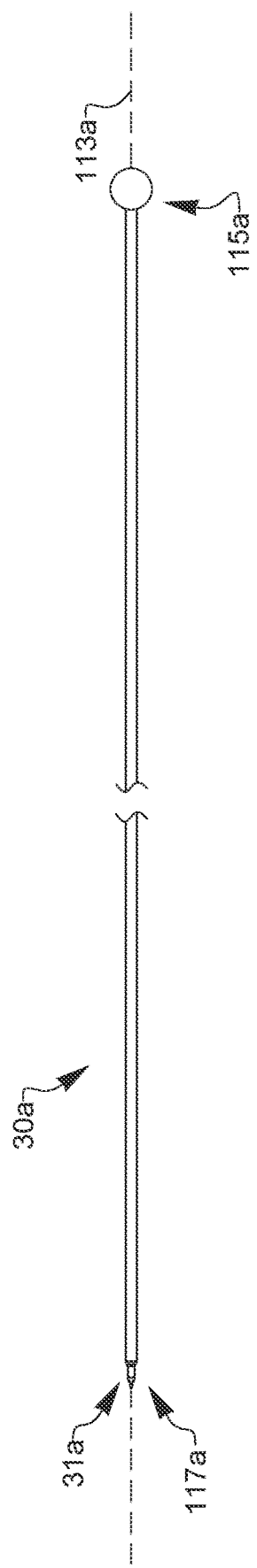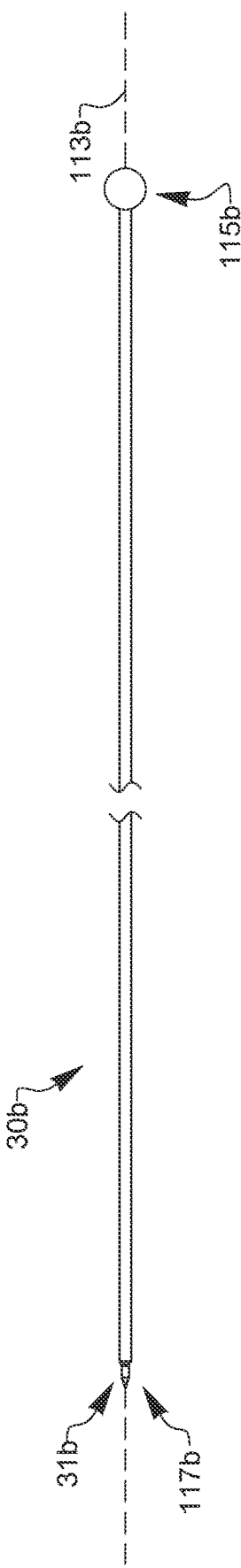

SPINAL ANNULOTOMY CLOSURE SEWING DEVICE

CROSS-REFERENCE TO RELATED APPLICATIONS

This application claims the benefit of U.S. Provisional Patent Application No. 63/314,889, filed Feb. 28, 2022, which is incorporated by reference herein in its entirety.

BACKGROUND OF THE INVENTION

The vertebral column, also known as the backbone or spine, is part of the axial skeleton. An intervertebral disc (or intervertebral fibrocartilage) lies between adjacent vertebrae in the vertebral column. Each intervertebral disc forms a fibrocartilaginous joint (a symphysis), to allow slight movement of the vertebrae, to act as a ligament to hold the vertebrae together, and to function as a shock absorber for the spine. Each intervertebral discs consist of an outer fibrous ring, the annulus fibrosus, that surrounds an inner gel-like center, the nucleus pulposus.

A spinal disc herniation, commonly referred to as a slipped disc, can happen when unbalanced mechanical pressures substantially deform the annulus fibrosus, allowing part of the nucleus pulposus to obtrude. Disc herniation commonly occurs during peak physical performance, during traumas, or as a result of chronic deterioration that is typically accompanied with poor posture. Both the deformed annulus and the gel-like material of the nucleus pulposus can be forced laterally or posteriorly, distorting local muscle function and putting pressure on nearby nerves. Such pressure may give symptoms typical of nerve root entrapment, which can vary between paresthesia, numbness, chronic and/or acute pain, either locally or along the dermatome served by the entrapped nerve, loss of muscle tone and decreased homeostatic performance.

Treatment of a herniated disc may involve removal (discectomy) of the herniated nucleus pulposus material by an incision through the annulus fibrosus (annulotomy) to relieve the problematic nucleus pulposus. Following the removal of the nucleus pulposus, the incision through the annulus fibrosus must be closed. However, there is little currently available technology used with minimally invasive procedures to close the annulus.

BRIEF SUMMARY

A device includes a housing portion having a grip portion adapted to be grasped by a hand of a user, and an actuation lever pivotably coupled to a first portion of the housing portion, the actuation lever configured to be pivoted between a first actuation lever position and a second actuation lever position by a user grasping the grip portion of the housing. The device also includes a shaft extending along a shaft axis from a proximal end to a distal end, wherein the proximal end of the shaft is coupled to a second portion of the housing portion. The device further includes a first needle extending along a first needle axis from a proximal end to a distal end, wherein at least a portion of the first needle extends through an interior portion of the shaft. A first needle tip is disposed at the distal end of the first needle, and the proximal end of the first needle is configured to be selectively coupled to a coupling portion of the actuation lever such that when the actuation lever is in the first actuation lever position, the first needle is in a first needle position, and when the actuation lever is in the second actuation lever position, the first needle is in a second needle position. The device additionally includes a second needle extending along a second needle axis from a proximal end to a distal end, wherein at least a portion of the second needle extends through the interior portion of the shaft. A second needle tip is disposed at the distal end of the second needle, and wherein the proximal end of the second needle is configured to be selectively coupled to the coupling portion of the actuation lever such that when the actuation lever is in the first actuation lever position, the second needle is in a first needle position, and when the actuation lever is in the second actuation lever position, the second needle is in a second needle position. The device also includes a selection lever coupled to a portion of the housing, the selection lever being pivotable from a first selection lever position and a second selection lever position, wherein in the first selection lever position, the proximal end of the first needle is coupled with the coupling portion of the actuation lever, and in the second selection lever position, the proximal end of the second needle is coupled with the coupling portion of the actuation lever.

The device additionally includes a distal end assembly coupled to the distal end of the shaft, the distal end assembly comprising a base portion extending from a proximal end to a distal end along the shaft axis, the base portion being partially defined by a base first lateral edge that extends from a proximal end at the proximal end of the base portion to a distal end at the distal end of the base portion, wherein the distal end of the base first lateral edge is a first distance from the shaft axis. The base portion is also partially defined by a base second lateral edge that extends from a proximal end at the proximal end of the base portion to a distal end at the distal end of the base portion, wherein the distal end of the base second lateral edge is the first distance from the shaft axis. The base portion further partially defined by a base first transverse edge that extends from a first end at or adjacent to the distal end of the base first lateral edge to a second end in a direction normal to the shaft axis, and a base second transverse edge that extends from a first end at or adjacent to the distal end of the base second lateral edge to a second end in a direction normal to the shaft axis. The distal end assembly also includes a support portion that extends from a proximal end to a distal end along the shaft axis such that the proximal end of the support portion is disposed at the distal end of the base portion, the support portion at least partially defined by a support first lateral edge disposed a second distance from the shaft axis, the support first lateral edge extending from a proximal end to a distal end, wherein the proximal end of the support first lateral edge being at or adjacent to the second end of the base first transverse edge. The support portion also at least partially defined by a support second lateral edge disposed the second distance from the shaft axis, the support second lateral edge extending from a proximal end to a distal end, wherein the proximal end of the support second lateral edge being at or adjacent to the second end of the base second transverse edge, with the first distance being greater than the second distance. The distal end assembly also includes a receiver portion disposed at or adjacent to the distal end of the support portion such that the receiver portion extends in a direction normal to the shaft axis, the receiver portion at least partially defined by a receiver first transverse edge that extends from a first end to a second end, the second end of the receiver first transverse edge being at or adjacent to the distal end of the support first lateral edge, the receiver first transverse edge extending normal to the shaft axis. The receiver portion also at least partially defined by a receiver second transverse edge that extends from a first end to a second end, the second end of the receiver second transverse edge being at or adjacent to the distal end of the support second lateral edge, the receiver second transverse edge extending normal to the shaft axis. The receiver first transverse edge, the support first lateral edge, and the base first transverse edge cooperate to define a first tissue bite area, and the receiver second transverse edge, the support second lateral edge, and the base second transverse edge cooperate to define a second tissue bite area. When the selection lever is in the first selection lever position, and when the actuation lever is pivoted from the first actuation lever position to the second actuation lever position, the first needle tip of the first needle extends from a first position, in which the first needle tip is proximal to the base first transverse edge, across the first tissue bite area to a second position in which the first needle tip is at least partially disposed within a first ferrule recess of the receiver portion such that the first needle tip is distal to the receiver first transverse edge. When the selection lever is in the second selection lever position, and when the actuation lever is pivoted from the first actuation lever position to the second actuation lever position, the second needle tip of the second needle extends from a first position, in which the second needle tip is proximal the base second transverse edge, across the second tissue bite area to a second position in which the second needle tip is at least partially disposed within a second ferrule recess of the receiver portion such that the second needle tip is distal to the receiver second transverse edge.

BRIEF DESCRIPTION OF THE DRAWINGS

FIG. 3A is side view of a distal end assembly of the embodiment of the device of FIG. 1A;

FIG. 3B is a top view of the distal end assembly of the embodiment of the device of FIG. 1A with the first needle in a first needle position and with the second needle in a second needle position;

FIGS. 4A to 4F are various views of a second embodiment of a distal end assembly;

FIG. 6A is a side view of an embodiment of a first needle of the device of FIG. 1A;

FIG. 6B is a side view of an embodiment of a second needle of the device of FIG. 1A;

DETAILED DESCRIPTION OF THE INVENTION

Figure 1A:
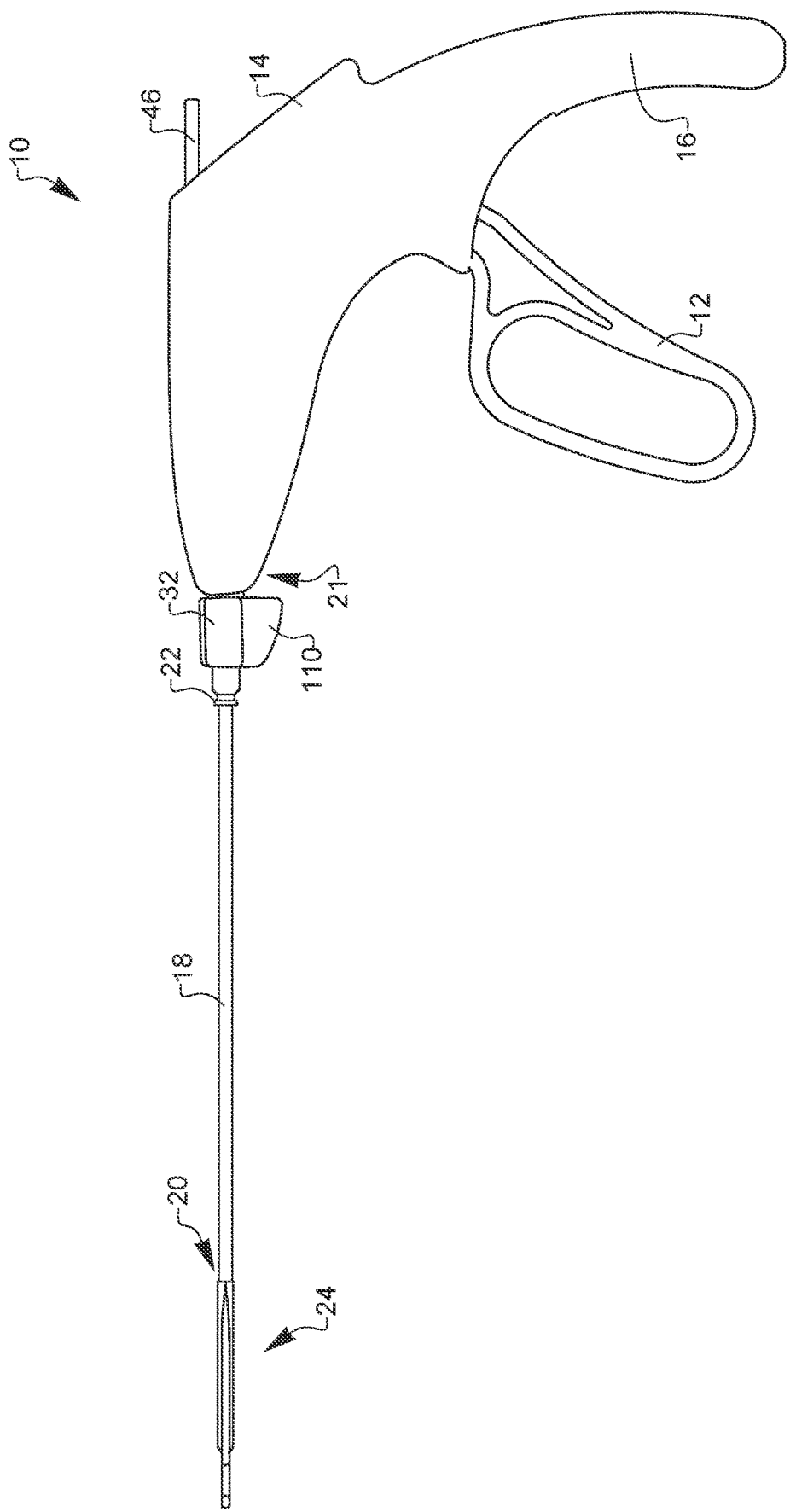
FIG. 1A is a first side view of an embodiment of a device with an actuation lever in a first actuation lever position.
Figure 1B:
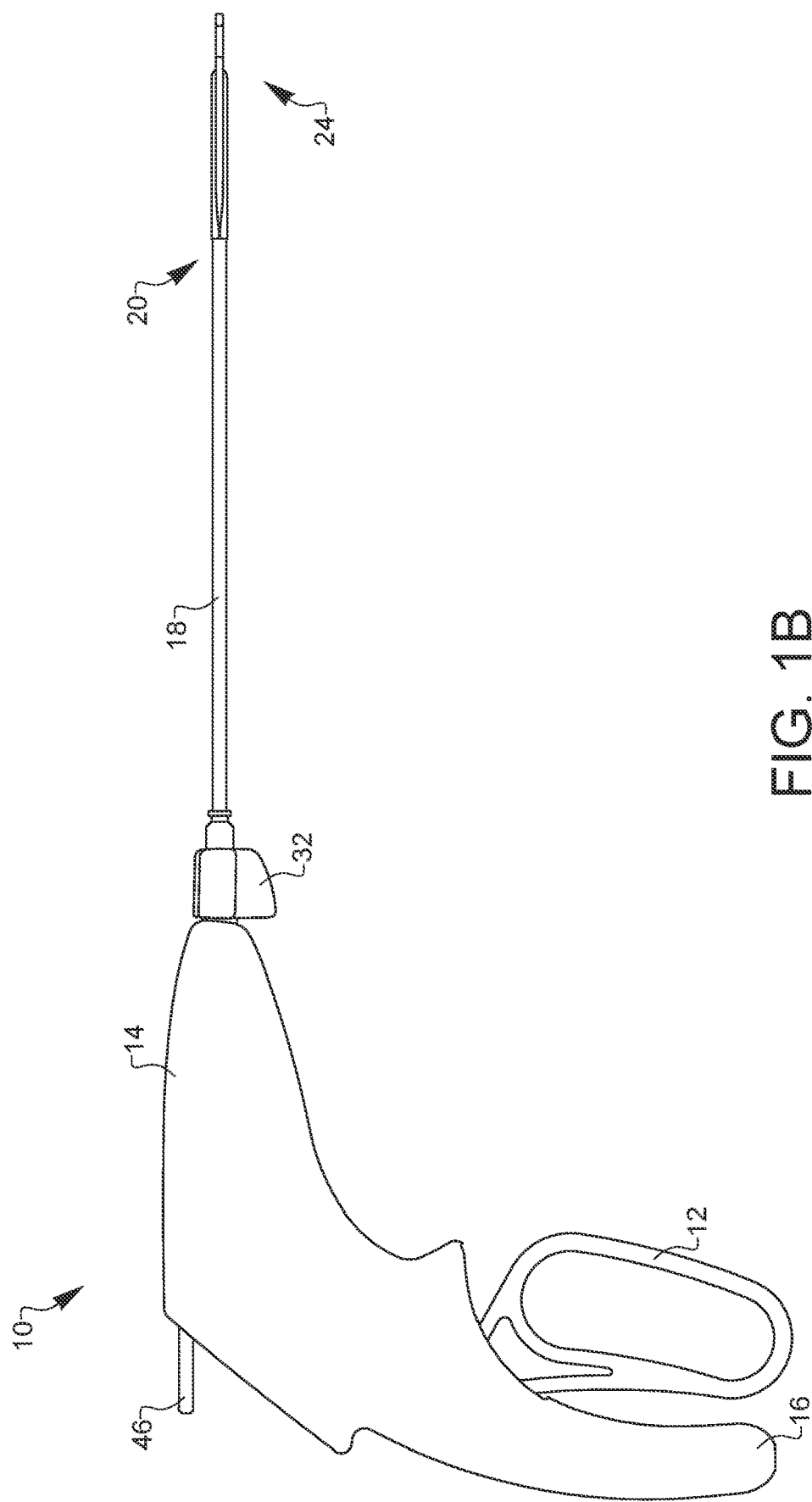
FIG. 1B is a second side view of the embodiment of the device of FIG. 1A with the actuation lever in a second actuation lever position.

FIGS. 1A and 1B illustrate an embodiment of a device 10 which may be used to, inter alia, close an incision through the annulus fibrosus that is typically made in procedures to treat a herniated disc. This device 10 provides for easy and gentle insertion through the incision, allows for a 90 degree rotation within the treatment area, and ferrule pick up and suture release from the tip when suturing. The device 10 also has a needle selector that allows the surgeon to take individual bites when approximating the annular tissue.

Figure 2A:
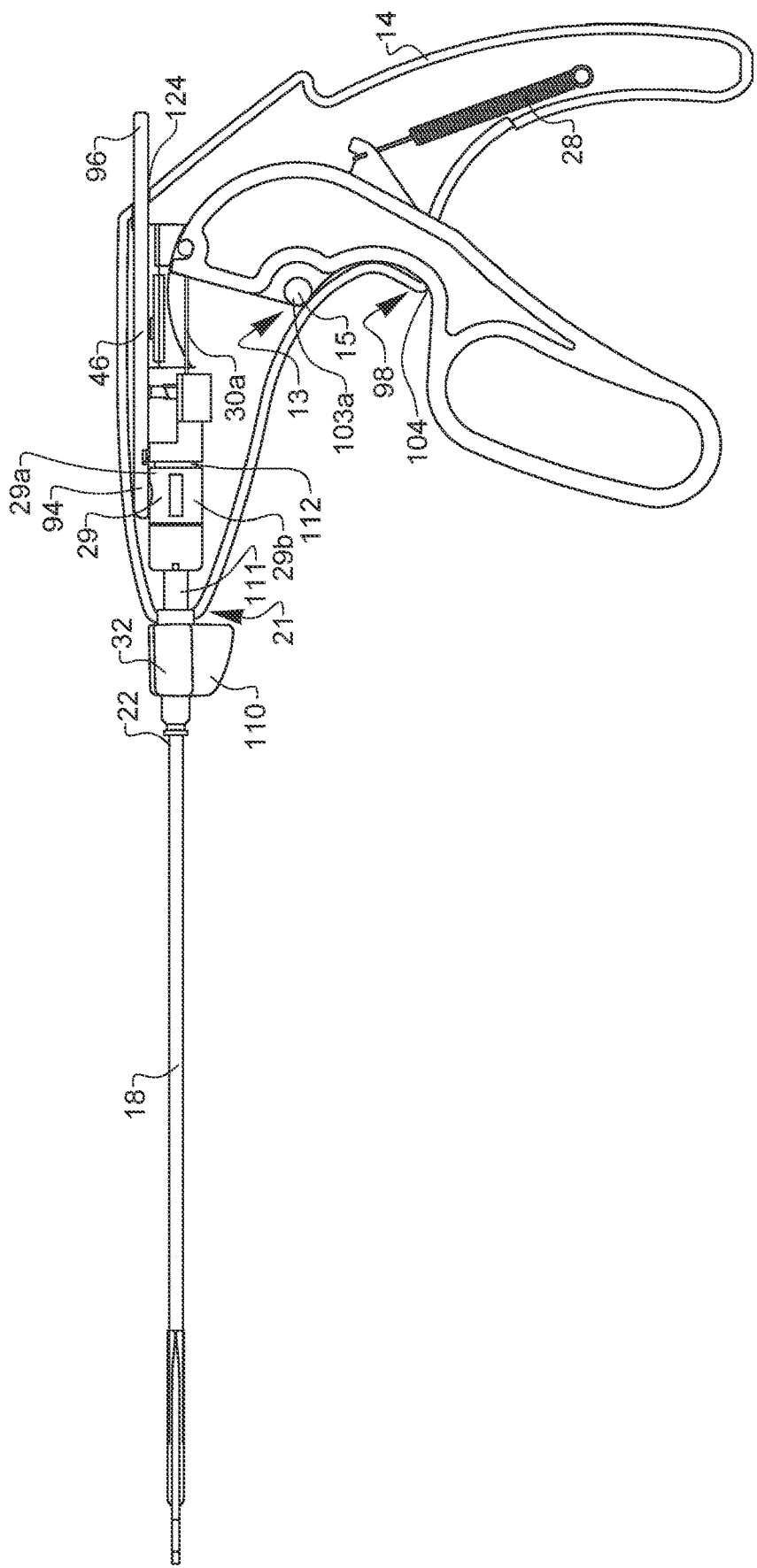
FIG. 2A is a side view of the embodiment of the device of FIG. 1A with a first portion of the housing portion omitted for clarity.
Figure 2B:
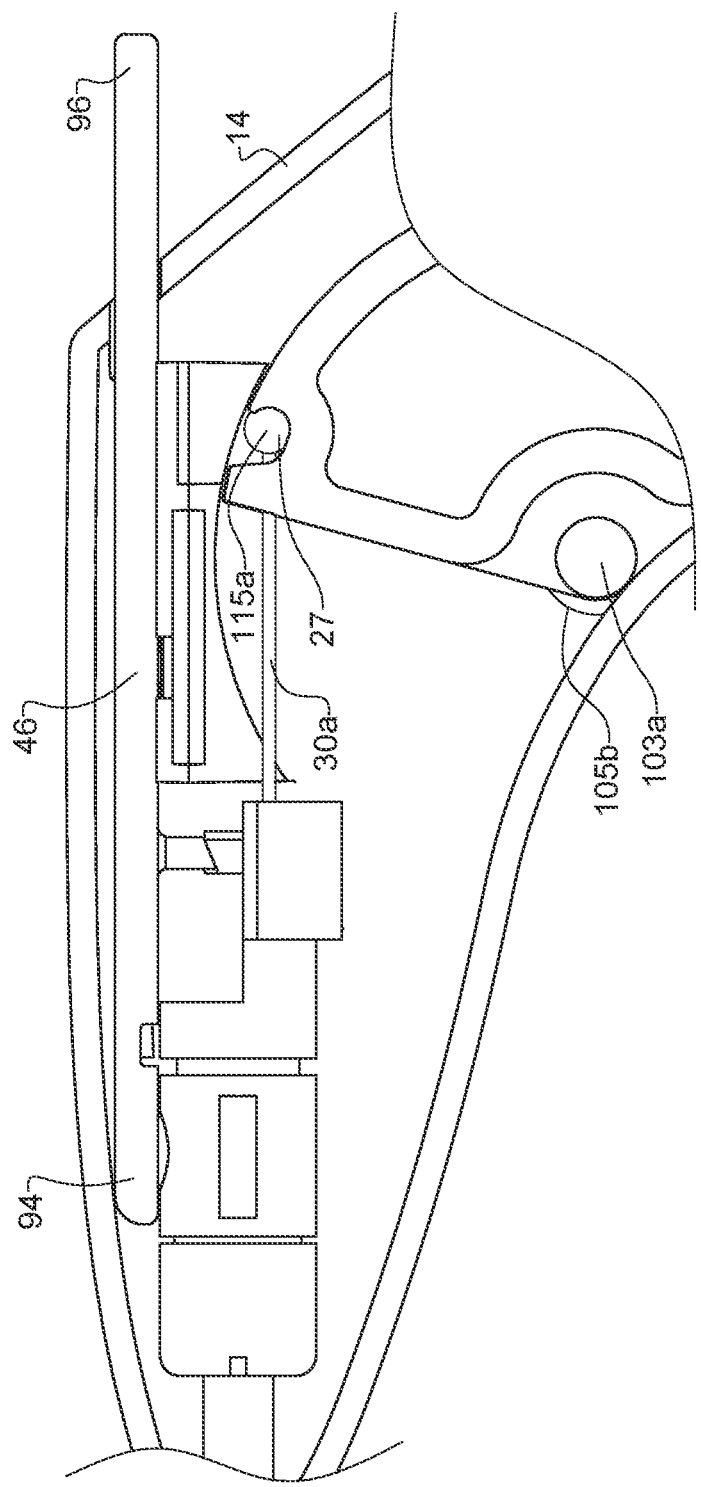
FIG. 2B is a detailed side view of FIG. 2A.

Turning to the side view of FIG. 1A, the device 10 includes the housing portion 14 having a grip portion 16 that is adapted to be grasped by a user to engage and displace an actuation lever 12 from a first lever position (illustrated in FIG. 1A) to a second lever position (illustrated in FIG. 1B). With reference to FIG. 2A (in which a portion of the housing portion 14 is omitted for clarity), a first portion 13 of the actuation lever 12 may be rotatably coupled to the housing portion 14 at a first portion 15 (e.g., a pivot point) of the housing portion 14 such that the actuation lever 12 pivots between the first lever position to the second lever position about the pivot point 15. The actuation lever 12 may pivot about a pivot axis that may extend through the pivot point 15 and may be normal to a shaft axis 19 that extends along the shaft 18 that is coupled to the housing portion 14. In particular, the first portion 13 of the actuation lever 12 may be a pair of aligned bosses 103a, 103b (103b not shown, with 103a illustrated in FIG. 2A) that are received into corresponding cylindrical internal walls 105a, 105b (105a not shown, 105b illustrated in FIG. 2B, in which a portion of the housing portion 14 is omitted for clarity) that are each formed on a corresponding interior portion of the housing portion 14 at the pivot point 15 of the housing portion 14. As shown in FIG. 2A, a portion 104 of the actuation lever 12 may contact a portion 98 of the housing portion 14 when the actuation lever 12 is in the first lever position to prevent the actuation lever 12 from overextending beyond the first lever position. A first end of a spring 28 may be coupled to a portion of the actuation lever 12 and a second end of the spring 28 may be coupled to a portion of the interior portion of the housing portion 14 such that the actuation lever 12 is biased into the first lever position by the spring 28.

Referring to FIG. 1A, the device 10 includes the shaft 18 that extends from a proximal end 22 to a distal end 20 along the shaft axis 19, and the shaft axis 19 may be linear. One or more portions of the shaft 18 may be rotatably coupled to a second portion 21 of the housing portion 14 such that the shaft 18 rotates relative to a housing portion 14 about the shaft axis 19. However, in some embodiments, the shaft 18 may be fixed relative to the housing portion 14. The shaft 18 may be rigid, but in other embodiments, the shaft 18 may be flexible or may have one or more portions that are flexible.

The shaft 18, or one or more portions of the shaft 18, may have the general shape of an elongated hollow tube having an interior surface 108 (illustrated in FIG. 3C) that defines an interior portion 109 that extends from the proximal end 22 to the distal end 20 of the shaft 18. The shaft 18 and the interior surface 108 may have any suitable cross-sectional shape or combination of shapes normal to the shaft axis 19. For example, the shaft 18 may have the general shape of an elongated cylinder, and the interior surface 108 may have a circular cross-sectional shape when viewed normal to the shaft axis 19.

Referring to FIG. 1A, a rotation knob 32 may be coupled to the shaft 18 such that rotating the rotation knob 32 may rotate the shaft 18 about the shaft axis 19. The rotation knob 32 may be coupled to a portion of the shaft 18 that is adjacent to the proximal end 22 of the shaft 18 and/or may be coupled to the portion of the shaft 18 that is distal to the portion of the housing portion 14 to which the shaft 18 is coupled. All or a portion of the rotation knob 32 may also be coupled to a portion of the housing portion 14, such as the second portion 21 of the housing portion 14. The rotational knob 32 may be configured to simultaneously rotate the shaft 18 and the first needle 31a and the second needle 31b that are each disposed at least partially within the interior portion 109 (illustrated in FIG. 3C) of the shaft 18. The rotation knob 32 can have any suitable shape, and in some embodiments, may be formed as a unitary portion of the shaft 18 itself. The rotation knob 32 may also include a direction indicator 110 that may be fin or protrusion that correlates with a direction of the distal end assembly 24 such that the operator of the device 10 can readily orient the housing portion 14 such that the distal end assembly 24 faces a desired direction. Because it may not always be possible or ergonomically practical for a surgeon to rotate the housing portion 14 of the device, embodiments having a rotatable shaft 18 may offer more orientation flexibility to the surgeon, thereby enabling tissue and prosthetic protection.

With reference to FIG. 2A, a portion 111 of the rotation knob 32 and/or a portion of the shaft 18 (e.g., a portion of the proximal end 22 of the shaft 18) may extend into the interior of the housing portion 14 and the portion 111 of the rotation knob 32 (and/or the portion of the shaft 18) may include two or more facets 112 (described and illustrated in U.S. Pat. No. 10,939,904, the contents of which is incorporated by reference herein in its entirety). The facets 112 may be planar circumferential surfaces of the portion 111, and the facets 112 may cooperate to form a polygonal cross-sectional shape (e.g., a hexagon, octagon, decagon, or dodecagon) when viewed along the shaft axis 19. In other embodiments, the facets 112 may be recesses, bumps, and/or angled edges. The facets 112 may be configured to engage corresponding engagement surfaces of a constraint assembly 29 that is disposed around the facets 112, and the engagement surfaces may correspond in cross-sectional shape with the facets 112. The constraint assembly 29 may be fixedly coupled to one or more interior portions of the housing portion 14. The constraint assembly 29 may include an upper constraint 29a and a lower constraint 29b that is coupled to the upper constraint 29a to form the constraint assembly 29. The constraint assembly 29 may be made from an injection-molded plastic material that may deform under stress.

When each facet 112 is flat against a corresponding engagement surfaces of the constraint assembly 29, rotation of the shaft 18 (to which the rotation knob 32 is coupled) within the constraint assembly 29 is resisted when a torque is applied to the shaft 18 that is below a threshold strength. However, when a sufficiently strong torque is applied to the shaft 18, the rotation of the facets 112 causes the corners between adjacent facets 112 to apply a force on the engagement surfaces of the constraint assembly 29, thereby deflecting or deforming the engagement surfaces and allowing the facets 112 and the shaft 18, to rotate relative to the engagement surfaces of the constraint assembly 29 until the next adjacent facet is flat against the corresponding engagement surface of the constraint assembly 29, thereby allowing the shaft 18 to rotate in specific increments that correspond to the angular spacing of the facets 112 about the shaft axis 19. The mating of the facets 112 with the engagement surfaces of the constraint assembly 29 may be felt by the user, thereby enabling indexing of the shaft along specific rotation positions.

With reference to FIG. 6A, the device 10 includes a first needle 30a extending along a first needle axis 113a from a proximal end 115a to a distal end 117a, and the first needle axis 113a may be linear. At least a portion of the first needle 30a extends through the interior portion 109 of the shaft 18 and the proximal end 115a may extend into the interior of the housing portion 14. A first needle tip 31a is disposed at the distal end 117a of the first needle 30a, and the first needle tip 31a may converge to a sharp point such that the distal end 117a is configured and shaped to pierce tissue that may be disposed in the first tissue bite area 35 defined in the distal end assembly 24 when the first needle 31a extends from a first needle position (i.e., a retracted position illustrated in FIGS. 3B and 3C) to a second needle position (i.e., an extended position illustrated in FIGS. 3D and 3E), as will be described in more detail in a following section. The proximal end 115a of the first needle 30a may be configured to be selectively coupled to a coupling portion 27 (illustrated in FIG. 2B) of the actuation lever 12 such that when the actuation lever 12 is in the first actuation lever position, the first needle is in the first needle position, and when the actuation lever 12 is in the second actuation lever position, the first needle is in the second needle position. The proximal end 115a of the first needle 30a may be selectively coupled to a coupling portion 27 of the actuation lever 12 in any suitable manner. For example, the proximal end 115a of the first needle 30a may have a spherical portion that may be received into a socket portion 27 of the of the actuation lever 12, as will be described in more detail in a following section. The first needle 30a may be fabricated from one or more materials that allows the first needle 30a to slightly bend within the distal end assembly 24.

Turning to FIG. 6B, the device 10 also includes a second needle 30b that may be identical or substantially identical to the first needle 30a. In particular, the second needle 30b may extend along a second needle axis 113b from a proximal end 115b to a distal end 117b, and the second needle axis 113b may be linear. At least a portion of the second needle 30b extends through the interior portion 109 (see FIG. 3C) of the shaft 18 and the proximal end 115b may extend into the interior of the housing portion 14. A second needle tip 31b is disposed at the distal end 117b of the second needle 30b, and the second needle tip 31b may converge to a sharp point such that the second needle tip 31b is configured and shaped to pierce tissue that may be disposed in the second tissue bite area 39 defined in the distal end assembly 24 when the second needle 31b extends from a first needle position (i.e., a retracted position illustrated in FIGS. 3D and 3E) to a second needle position (i.e., an extended position illustrated in FIG. 3B), as will be described in more detail in a following section. The proximal end 115b of the second needle 30b may be configured to be selectively coupled to the coupling portion 27 (illustrated in FIG. 2B) of the actuation lever 12 such that when the actuation lever 12 is in the first actuation lever position, the second needle is in the first needle position, and when the actuation lever 12 is in the second actuation lever position, the second needle is in the second needle position. The proximal end 115a of the second needle 30a may be selectively coupled to a coupling portion 27 of the actuation lever 12 in any suitable manner. For example, the proximal end 115a of the second needle 30a may have a spherical portion that may be received into a socket portion 27 of the of the actuation lever 12, as will be described in more detail in a following section. The second needle 30b may be fabricated from one or more materials that allows the second needle 30b to slightly bend within the distal end assembly 24.

With reference to FIG. 1A, the device 10 may include the distal end assembly 24 coupled or fixedly secured to the distal end 20 of the shaft 18 or a point adjacent to the distal end 20 of the shaft 18. The distal end assembly 24 may extend along or generally along the shaft axis 19, which may be parallel to the X-axis of the reference coordinate system of FIGS. 3A and 3B, from a proximal end 58 of the distal end assembly 24 to a distal end 59 of the distal end assembly 24. The distal end assembly 24 may include a base portion 36, a support portion 48, and a receiver portion 56.

Figure 3C:
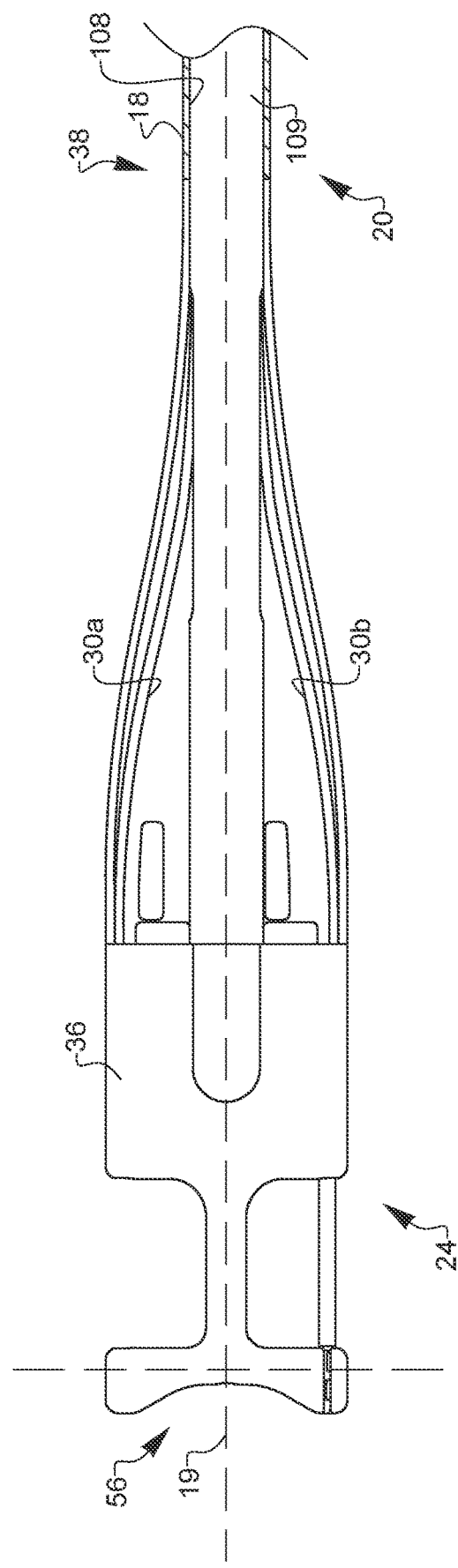
FIG. 3C is the top view of the distal end assembly of FIG. 3B with a portion of the distal end assembly omitted for clarity.
Figure 3E:
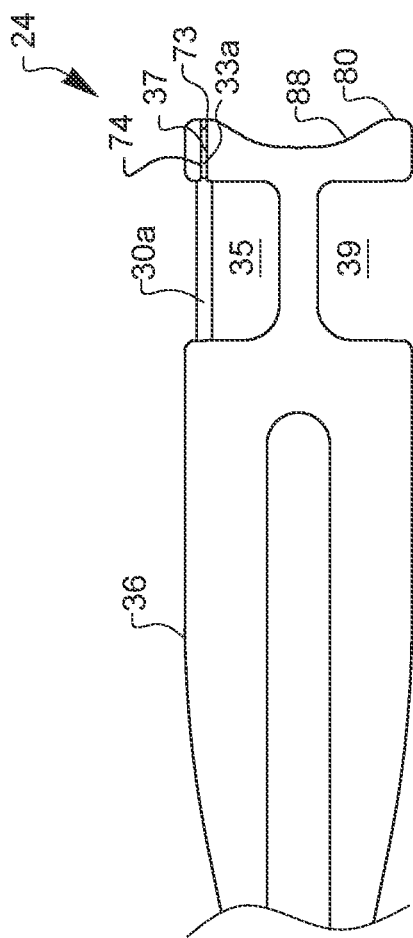
FIG. 3E is a side view of the distal end assembly of FIG. 3D.

As illustrated in FIG. 3B, the base portion 36 of the distal end assembly 24 may extend from a proximal end 38 (illustrated in FIG. 3C) to a distal end 40 along the shaft axis 19, and the base portion 36 may be partially defined by a base first lateral edge 42 that extends from a proximal end at the proximal end 38 of the base portion 36 to a distal end at the distal end 40 of the base portion 24. The base first lateral edge 42 may include a linear portion 118 that extends from the distal end of the base first lateral edge 42 to an intermediate point 120 between the proximal and distal ends of the base first lateral edge 42. The linear portion 118 may extend parallel or generally parallel to the shaft axis 19 (or along the X-axis of the reference coordinate system of FIG. 3B). A proximal portion of the base portion 36 may have a gradually reducing width (along the Y-axis of the reference coordinate system of FIG. 3B) such that the base first lateral edge 42 converges towards the shaft axis 19 as the base first lateral edge 42 extends proximally from the intermediate point 120 to the proximal end 38 of the base portion 38. Specifically, the base first lateral edge 42 may include a contoured portion 122 that extends from the intermediate point 120 to the proximal end of the base first lateral edge 42 and/or the proximal end 38 of the base portion 36. The contoured portion 122 may define one or more internal features that are configured to allow the distal end 117a of the first needle 30a to gradually transition in position away from the shaft axis 19 to allow for proper alignment of the distal end 117a of the first needle 30a as the first needle 30a displaces from the first needle position to the second needle position. The distal end of the base first lateral edge 42 and/or the linear portion 118 may be a first distance D1 from the shaft axis 19. The base portion 36 may be further defined by a base first transverse edge 64 that extends from a first end at or adjacent to the distal end of the base first lateral edge 42 to a second end, and the base first transverse edge 64 may extend from the first end to the second end in a direction normal to the shaft axis 19 (or along the Y-axis of the reference coordinate system of FIG. 3B).

Still referring to FIG. 3B, the base portion 36 may be partially defined by a base second lateral edge 44 that may be symmetrically disposed about the shaft axis 19 from the base first lateral edge 42 such that the base second lateral edge 44 extends from a proximal end at the proximal end 38 (illustrated in FIG. 3C) of the base portion 36 to a distal end at the distal end 40 of the base portion 24, and the base second lateral edge 44 may be a mirror image of the base first lateral edge 42. Specifically, the base second lateral edge 44 may include a linear portion 126 that extends from the distal end of the base second lateral edge 44 to an intermediate point 127 between the proximal and distal ends of the base second lateral edge 44. The linear portion 126 may extend parallel or generally parallel to the shaft axis 19 (or along the X-axis of the reference coordinate system of FIG. 3B). As with the first lateral edge 42, the base second lateral edge 44 converges towards the shaft axis 19 as the base second lateral edge 44 extends proximally from the intermediate point 120 to the proximal end 38 of the base portion 38. In particular, the base second lateral edge 44 may also include a contoured portion 128 that extends from the intermediate point 127 to the proximal end of the base second lateral edge 44 and/or the proximal end 38 of the base portion 36. The contoured portion 128 may define one or more internal features that are configured to allow the distal end 117b of the second needle 30b to gradually transition in position away from the shaft axis 19 to allow for proper alignment of the distal end 117b of the second needle 30b as the second needle 30b displaces from the first needle position to the second needle position. The distal end of the base second lateral edge 44 and/or the linear portion 126 may any suitable distance from the shaft axis 19, such as the first distance D1 from the shaft axis 19. The base portion 36 may be further defined by a base second transverse edge 66 that extends from a first end at or adjacent to the distal end of the base second lateral edge 44 to a second end, and the base second transverse edge 66 may extend from the first end to the second end in a direction normal to the shaft axis 19 (or along the Y-axis of the reference coordinate system of FIG. 3B) and aligned with (i.e., extending along an axis that is aligned with) the base first lateral edge 42.

As illustrated in FIG. 3B, the support portion 48 of the distal end assembly 24 may extend from a proximal end 49 to a distal end 50 along the shaft axis 19 such that the proximal end 49 of the support portion is disposed at the distal end 40 of the base portion 36. The support portion 48 may be at least partially defined by a support first lateral edge 52 that may be linear or substantially linear and may extend along the X-axis of the reference coordinate system of FIG. 3B). The support first lateral edge 52 may be disposed a second distance D2 from the shaft axis 19, and the second distance D2 may be less than the first distance D1. The support first lateral edge 52 may extend from a proximal end to a distal end, and the proximal end of the support first lateral edge 52 may be disposed at or adjacent to the second end of the base first transverse edge 64. The support portion 48 may also be at least partially defined by a support second lateral edge 54 that may be linear or substantially linear and may extend along the X-axis of the reference coordinate system of FIG. 3B. The support second lateral edge 54 may be disposed any suitable distance from the shaft axis 19, such as the second distance D2 from the shaft axis 19 such that the shaft axis 19 longitudinally bisects the support portion 48. The support second lateral edge 54 may extend from a proximal end to a distal end, and the proximal end of the support second lateral edge 54 may be disposed at or adjacent to the second end of the base second transverse edge 66, with the first distance being greater than the second distance.

Still referring to FIG. 3B, the distal end assembly 24 may include the receiver portion 56 disposed at or adjacent to the distal end 50 of the support portion 48 and/or at or adjacent to the distal end 59 of the distal end assembly 24. The receiver portion 56 may be elongated and may extend or generally extend in a direction normal to the shaft axis 19 and/or along the Y-axis of the reference coordinate system of FIG. 3B. The receiver portion 56 may be at least partially defined by a receiver first transverse edge 60 that extends from a first end to a second end, and the receiver first transverse edge 60 that may be linear or substantially linear and may extend along the Y-axis of the reference coordinate system of FIG. 3B. The second end of the receiver first transverse edge 60 may be disposed at or adjacent to the distal end of the support first lateral edge 52. The receiver portion 56 may also be defined by a first lateral edge 68 that may extend from a proximal end to a distal end along or generally along the X-axis of the reference coordinate system of FIG. 3B. The proximal end of the first lateral edge 68 may be at or adjacent to the first end of the receiver first transverse edge 60. The first lateral edge 68 may be disposed any suitable distance from the shaft axis 19, such as the first distance D1 from the shaft axis 19 such that the first lateral edge 68 and the linear portion 118 of the base first lateral edge 42 are aligned along an axis parallel to the X-axis of the reference coordinate system of FIG. 3B.

The receiver portion 56 may also be at least partially defined by a receiver second transverse edge 62 that extends from a first end to a second end, and the receiver second transverse edge 62 that may be linear or substantially linear and may extend along the Y-axis of the reference coordinate system of FIG. 3B. The receiver second transverse edge 62 may be aligned with (i.e., extend along an axis that is aligned with) the receiver first transverse edge 60. The second end of the receiver second transverse edge 62 may be disposed at or adjacent to the distal end of the support second lateral edge 54. The receiver portion 56 may also be defined by a second lateral edge 70 that may extend from a proximal end to a distal end along or generally along the X-axis of the reference coordinate system of FIG. 3B. The proximal end of the second lateral edge 70 may be at or adjacent to the first end of the receiver second transverse edge 62. The second lateral edge 70 may be disposed any suitable distance from the shaft axis 19, such as the first distance D1 from the shaft axis 19 such that the second lateral edge 70 and the linear portion 126 of the base second lateral edge 44 are aligned along an axis parallel to the X-axis of the reference coordinate system of FIG. 3B.

So configured, when viewed along the Z-axis of the reference coordinate system of FIG. 3A, the receiver first transverse edge 60 of the receiver portion 56, the support first lateral edge 52 of the support portion 48, and the base first transverse edge 64 cooperate to define the first tissue bite area 35. In addition, the receiver second transverse edge 62 of the receiver portion 56, the support second lateral edge 54 of the support portion 48, and the base second transverse edge 66 of the base portion 36 cooperate to define the second tissue bite area 39.

Figure 3F:
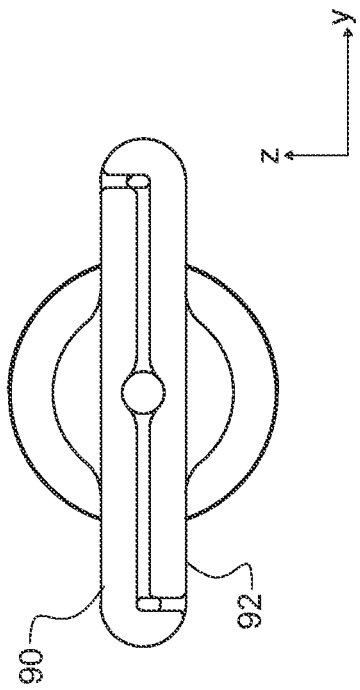
FIG. 3F is a front view of the distal end assembly of FIG. 3D.
Figure 3D:
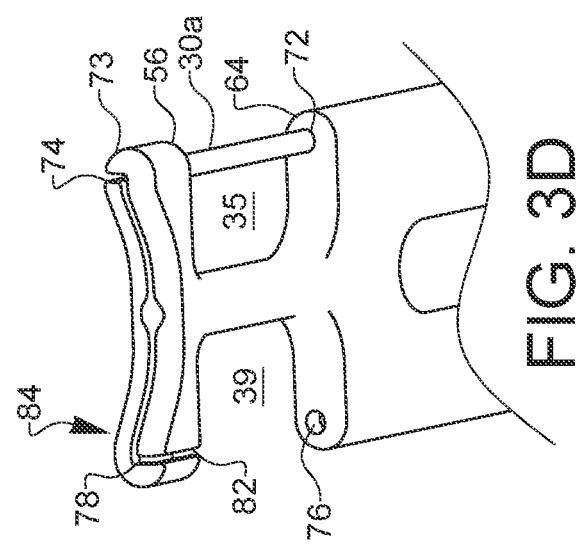
FIG. 3D is a perspective view of the distal end assembly of the embodiment of the device of FIG. 1A with the first needle in the second needle position and with the second needle in the first needle position.

As illustrated in FIGS. 3B and 3D, the base portion 36 may include a first needle aperture 72 disposed in a surface defined at least in part by the base first transverse edge 64, and an axis (see FIG. 3B) extending through the first needle aperture 72 may parallel to the X-axis and be disposed a distance slightly less than distance D1 such that the axis extending through the first needle aperture 72 is disposed adjacent to the first lateral edge 42 (or the linear portion 118) at the distal end 40 of the base portion 36. When the first needle 30a is in the first needle position (i.e., the retracted position illustrated in FIGS. 3B and 3C), the first needle tip 31a of the first needle 30a is disposed proximal to the surface defined at least in part by the first transverse edge 64 such that no portion of the first needle tip 31a of the first needle 30a is disposed or extends into the first tissue bite area 35. However, when the first needle tip 31a of the first needle 30a is displaced from the first needle position to the second needle position (i.e., the extended position illustrated in FIG. 3E), the first needle tip 31a of the first needle 30a extends through the first needle aperture 72 and into (and completely through) the first tissue bite area 35 such that in the second needle position, the first needle tip 31a of the first needle 30a extends at least partially into the first ferrule recess 37 formed in a portion of the receiver portion 56 to operatively engage a first ferrule 33a disposed in the first ferrule recess 37. The first ferrule 33a may be any ferrule that is configured to be secured to a portion of suture extending from a distal end of the first ferrule 33a and that is configured to be selectively coupled to and uncoupled from the first needle tip 31a via an interface (i.e., a channel) that inwardly extends from a proximal end of the first ferrule 33a, and the first ferrule 33a may be similar to the ferrule disclosed in U.S. Pat. No. 10,390,818, which issued on Aug. 27, 2019 and which is herein incorporated by reference in its entirety.

With reference to FIG. 3B, the first ferrule recess 37 may be an aperture that extends through a portion of the receiver portion 56, and an axis of the first ferrule recess 37 may be aligned with the axis of the first needle aperture 72 such that the axis of the first ferrule recess 37 and the axis of the first needle aperture 72 are both disposed an equal distance (in the direction of the Y-axis) from the shaft axis 19. The first ferrule recess 37 may extend entirely through the portion of the receiver portion 56 such that a proximal end of the first ferrule recess 37 is disposed on a surface at least partially defined by the receiver first transverse edge 60 of the receiver portion 56 and a distal end of the first ferrule recess 37 is disposed on a surface at least partially defined by a first exit edge 73 of the receiver portion 56. A first suture channel 74 may extend from the proximal end of the first ferrule recess 37 to the distal end the first ferrule recess 37 to allow suture (not shown) coupled to the distal end of the first ferrule 33a to be inserted into and removed from the first suture channel 74. A proximal end of the first ferrule 33a may be disposed at or adjacent to the proximal end of the first ferrule recess 37, and a distal end of the first ferrule 33a may be proximal to the first exit edge 73. The first ferrule recess 37 may be sized and configured to retain the first ferrule 33a when the first needle tip 31a of the first needle 30a is in the first needle position, but is configured to allow the first ferrule 33a to operatively couple to the first needle tip 31a of the first needle 30a when the first needle 30 displaces from the second needle position to the first needle position, thereby pulling the first ferrule 33a (and the suture coupled to the first ferrule 33a) through an aperture formed in the tissue disposed within the first tissue bite area 35. One or more locking or release mechanisms may be disposed at or adjacent to (and/or remote from) the first ferrule recess 37 to selectively retain and release the first ferrule 33a.

Referring again to FIGS. 3B and 3D, the base portion 36 may include a second needle aperture 76 disposed in a surface defined at least in part by the base second transverse edge 66, and an axis extending through the second needle aperture 76 may parallel to the X-axis and be disposed a distance slightly less than distance D1 such that the axis extending through the second needle aperture 76 is disposed adjacent to the second lateral edge 44 (or the linear portion 126) at the distal end of the base portion 36. When the distal end 31b of the second needle 30b is in the first needle position (i.e., the retracted position illustrated in FIGS. 3D and 3E), the distal end 31b of the second needle 30b is disposed proximal to the surface defined at least in part by the second transverse edge 66 such that no portion of the distal end 31*b* of the second needle 30*b* is disposed or extends into the second tissue bite area 39. However, when the distal end 31*b* of the second needle 30*b* is displaced from the first needle position to the second needle position (i.e., the extended position illustrated in FIG. 3B), the distal end 31*b* of the second needle 30*b* extends through the second needle aperture 76 and into (and completely through) the second tissue bite area 39 such that in the extended position, the distal end 31*b* of the second needle 30*b* extends at least partially into a second ferrule recess 78 formed in a portion of the receiver portion 56 to operatively engage a second ferrule 33*b* disposed in the second ferrule recess 78, and the second ferrule 33*b* may be identical to the first ferrule 33*a*.

As illustrated in FIG. 3B, the second ferrule recess 78 may be an aperture that extends through a portion of the receiver portion 56, and an axis of the second ferrule recess 78 may be aligned with the axis of the second needle aperture 76 such that the axis of the second ferrule recess 78 and the axis of the second needle aperture 76 are both disposed an equal distance (in the direction of the Y-axis) from the shaft axis 19. The second ferrule recess 78 may extend entirely through the portion of the receiver portion 56 such that a proximal end of the second ferrule recess 78 is disposed on a surface at least partially defined by the receiver second transverse edge 62 of the receiver portion 56 and a distal end of the second ferrule recess 78 is disposed on a surface at least partially defined by a second exit edge 80 of the receiver portion 56. A second suture channel 82 may extend from the proximal end of the second ferrule recess 78 to the distal end the second ferrule recess 78 to allow suture (not shown) coupled to a distal end the second ferrule 33*b* to be inserted into and removed from the second suture channel 82. A proximal end of the second ferrule 33*b* may be disposed at or adjacent to the proximal end of the second ferrule recess 78, and a distal end of the second ferrule 33*b* may be proximal to the second exit edge 80. The second ferrule recess 78 may be sized and configured to retain the second ferrule 33*b* when the distal end 31*b* of the second needle 30*b* is in the first needle position, but configured to allow the second ferrule 33*b* to operatively couple to the distal end 31*b* of the second needle 30*b* when the second needle 30*b* displaces from the second needle position to the first needle position, thereby pulling the second ferrule 33*b* (and the suture coupled to the second ferrule 33*b*) through an aperture formed in the tissue disposed within the second tissue bite area 39. One or more locking or release mechanisms may be disposed at or adjacent to (and/or remote from) the second ferrule recess 78 to selectively retain and release the second ferrule 33*b*. The second suture channel 82 may face a direction (when viewed along the X-axis) that is opposite to the first suture channel 74.

With reference to FIG. 3B, the receiver portion 56 may also be at least partially defined by a distal edge 84 that extends from an inward end of the first exit edge 73 to an inward end of the second exit edge 80, and the distal edge 84 may be arcuate or curved. Referring to FIG. 3D, a first surface groove 86*a* may be disposed through a surface that at least partially defines (or is at least partially defined by) the distal edge 84, and the first surface groove 86*a* may extend from the distal end of the first ferrule recess 37 to a central aperture 88 that extends through the surface along the shaft axis 11. A second surface groove 86*b* may be disposed through the surface that at least partially defines (or is at least partially defined by) the distal edge 84, and the second surface groove 86*b* may extend from the distal end of the second ferrule recess 78 to the central aperture 88.

With reference to FIGS. 3A and 3F, which is a view of the device 10 along the Y-axis of the reference coordinate system of FIG. 3B and along the X-axis of the reference coordinate system of FIG. 3B, respectively, the distal end assembly 24 may have a rectangular cross-sectional shape, and the distal end assembly 24 may have a first surface 90 that may be planar or substantially planar (e.g., parallel to the X-Y plane of the reference coordinate system of FIG. 3B) and a second surface 92 that may be planar or substantially planar (e.g., parallel to the X-Y plane of the reference coordinate system of FIG. 3B) and offset from the first surface 90 along the Z-axis.

Figures 7A, 7B, 7C:
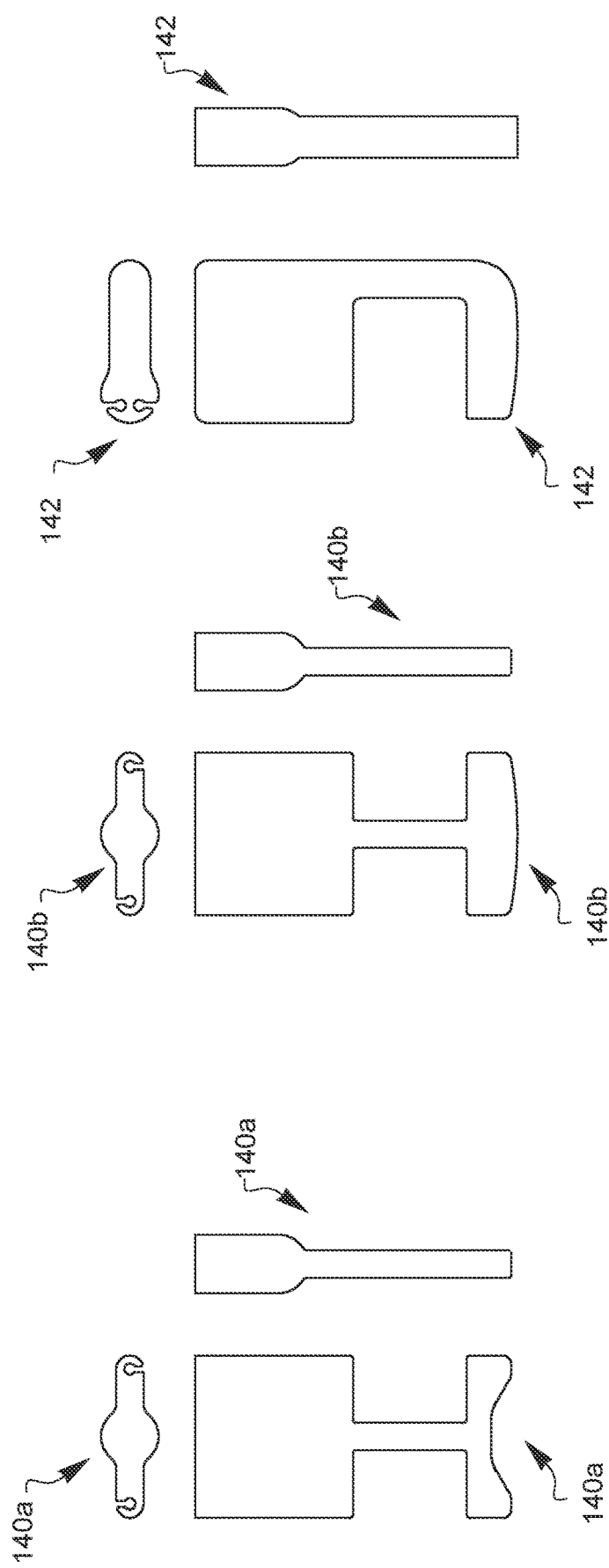
FIG. 7A are various views of a fourth embodiment of a distal end assembly.
FIG. 7B are various views of a fifth embodiment of a distal end assembly.
FIG. 7C are various views of a sixth embodiment of a distal end assembly.

In some embodiments, such as those illustrated in FIGS. 7A and 7B, the shape of the distal end assembly 140*a*, 140*b* may slightly vary from the embodiment described above. In another embodiment illustrated in FIG. 7C, only a single needle (and a single tissue gap) may be provided in the distal end assembly 142.

In some embodiments, the cross-sectional shape of the distal end assembly may have an X-shape (or a plus-shape) instead of the previously disclosed planar shape. Such an embodiment is illustrated in the embodiment of the distal end assembly 200 illustrated in FIGS. 4A to 4F, which illustrates an embodiment which includes a first portion that is identical to the embodiment of the distal end assembly 24 described above, and a second portion that is identical to the embodiment of the distal end assembly 24 described above, but disposed at a 90 degree angle to the first portion. The distal end assembly 200 may accommodate up to four needles (not shown) that may each extend from a first needle position to a second needle position individually or in synchronization with one or more other needles. When displaced from the first needle position to the second needle position, each needle may have a distal end that is configured to engage a ferrule (not shown) disposed in a corresponding ferrule recess of the plus-shaped receiver portion 202 and retract that ferrule though a corresponding one of four tissue gaps 205*a*, 205*b*, 205*c*, 205*d* defined by surfaces associated with the receiver portion 202, the support portion 204, and the base portion 206. A selection lever (not shown) may allow a user to select a needle or a group of needles to be coupled to the actuator lever 12 to be displaced from the first needle position to the second needle position.

Figure 5C:
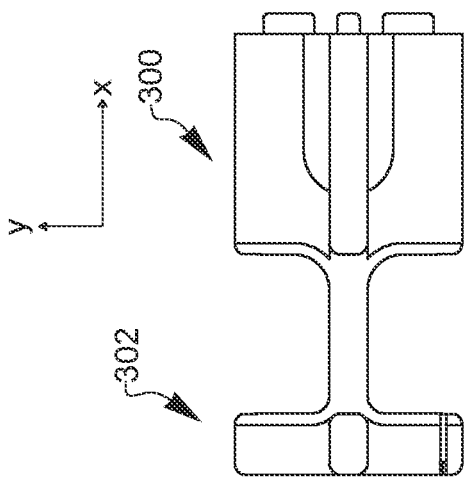
FIGS. 5A to 5E are various views of a third embodiment of a distal end assembly.
Figure 5B:
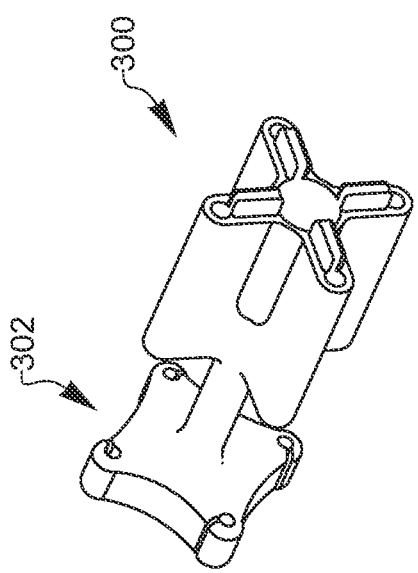
Figure 5A:
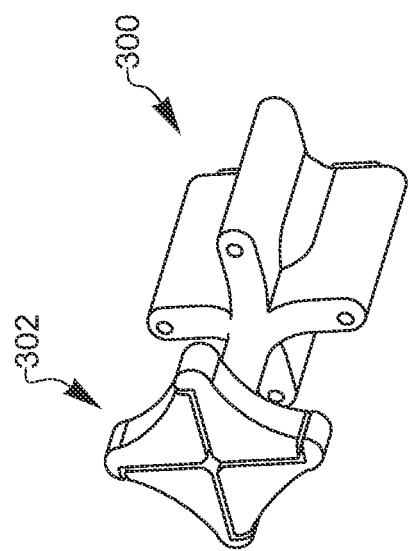
Figure 5E:
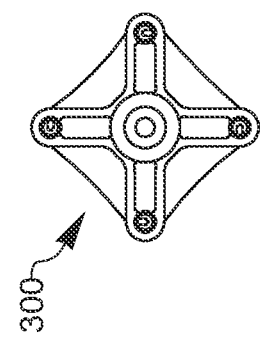
Figure 5D:
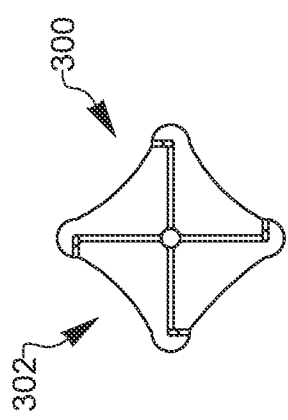

In another embodiment of the tip portion 300 illustrated in FIGS. 5A to 5E, the shape may be generally similar to the embodiment of the tip portion 100 illustrated in FIGS. 4A to 4F, with the exception that the receiver portion 302 does not have a plus-shape, but rather has a diamond shape when viewed along the X-axis of the reference coordinate system of FIG. 5C.

The distal end assembly 24, 100, 200 may be secured to the shaft 18 in any suitable manner. For example, one or more pins may secure the distal end assembly 24, 100, 200 to the distal end 20 of the shaft 18. The distal end assembly 24, 140*a*, 140*b*, 142, 200, 300 (i.e., the base portion 36, the support portion 48, and the receiver portion 56) may be a single, unitary part or an assembly of two or more parts. Each of the one or more needles 30*a* may be flexible to extend through the distal end assembly 24, 140*a*, 140*b*, 142, 200, 300 and into an interior portion 109 of the shaft 18, and each of the needles may curve to contour to the shape of a corresponding one of the base first lateral edge 42 or the base second lateral edge 44, and surfaces defining or at least partially defined by the base first lateral edge 42 or the base second lateral edge 44 may guide the needle along a desired path when displacing from a first needle position to a second needle position (or vice versa). The central aperture 88 may extend through the distal end assembly 24, 140a, 140b, 142, 200, 300 from the proximal end 58 to the distal end 59 such that central aperture 88 opens to the interior portion 109 of the shaft 18.

With reference to FIG. 2A, the device may additionally include a selection lever 46 that may be elongated and may extend along an axis from a first end 94 to a second end 96, and the selector lever 46 may be planar or substantially planar. The selection lever 46 (at or adjacent to the first end 94) may be rotatably or pivotably coupled to a portion of the housing portion 14 or a portion of the constraint assembly 29, such as by a journal, and the pivot axis may be normal to the shaft axis 19. The selection lever 46 may be displaced from a first selection lever position, in which only the first needle 30a is coupled to the actuator lever 12, to a second selection lever position, in which only the second needle 30b is coupled to the actuator lever 12. Thus, when the selection lever 46 is in the first selection lever position, only the first needle tip 31a of the first needle 30a is displaced from the first needle position to the second needle position when the actuator lever 12 is squeezed by a user, and only the first needle tip 31a of the first needle 30a is displaced from the second needle position to the first needle position when the actuator lever 12 is released. With the selector lever 46 is in the first position, the second needle 30b may remain in the first needle position when the actuator lever 12 is squeezed and/or released.

However, when the selection lever 46 is in the second selection lever position, only the distal end 31b of the second needle 30b is displaced from the first needle position to the second needle position when the actuator lever 12 is squeezed, and only the distal end 31b of the second needle 30b is displaced from the second needle position to the first needle position when the actuator lever 12 is released. With the selection lever 46 is in the second selection lever position, the first needle tip 31a of the first needle 30a may remain in the first needle position when the actuator lever 12 is squeezed and/or released.

A user may pivot the selection lever 46 by grasping a portion of the second end 94 that extends through a slot 124 formed in a proximal portion of the housing portion 14 and pivoting the selection lever 46 from a first selection lever position, in which only the first needle 30a is coupled to the actuator lever 12 to a second selection lever position, in which only the second needle 30b is coupled to the actuator lever 12.

Figure 2C:
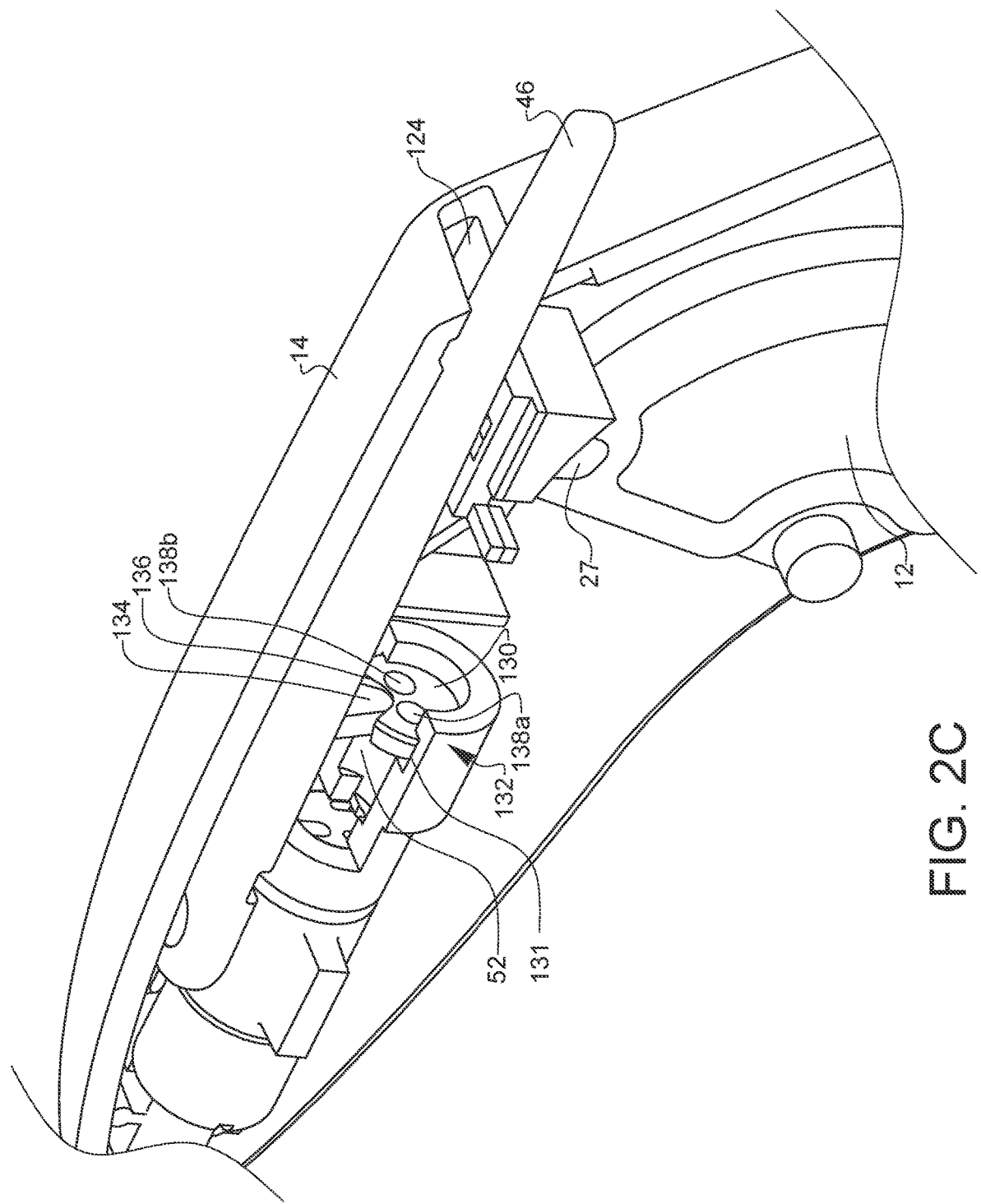
FIG. 2C is a perspective view of the embodiment of the device of FIG. 2A with a first needle and a second needle omitted for clarity.

The selection lever 46 may selectively engage (and disengage) a respective one of the proximal end 115a of the first needle 30a or the proximal end 115b of the second needle 30b with the coupling portion 27 (illustrated in FIG. 2B) of the actuation lever 12 in any suitable manner. For example, such a needle selection mechanism may be identical to that disclosed in U.S. Pat. No. 6,641,592 entitled "System for Wound Closure," which is incorporated herein by reference in its entirety. That is, with reference to FIG. 2C, a cam member 130 may be supported within a pocket 131 of an adapter 132 that is secured to an interior portion of the housing portion 14 such that the cam member 130 may rotate within the pocket 131 of the adapter 132 about a rotational axis that may be parallel to the shaft axis 19. The selection lever 46 may include a downwardly protruding member 134 that is received in a notch 136 of the cam member 130 to rotate cam member 30 in the pocket 131 of the adapter 32 as the selection lever 46 is moved left or right. The cam member 130 may include a first aperture 138a and a second aperture 138b, and a portion of the first needle 30a may extend through the first aperture 138a and a portion of the second needle 30b may extend through the second aperture 138b. To select the first needle 30a for engagement, the selection lever 46 is moved to the first selection lever position (e.g., the left) which rotates the cam member 130 to position the proximal end 115a of the first needle 30a "down" into engagement with the socket 27 of the actuator lever 12 while at the same time positioning the proximal end 115b of the second needle 30b "up" and above the socket 27 of the actuator lever 12. With the proximal end 115a of the first needle 30a so positioned within the socket 27 of the actuator lever 12, pivoting the actuator lever 12 from the first actuation lever position to the second actuation lever position advances the first needle 30a from the first needle position to the second needle position while the second needle 30b that is not engaged with the socket 27 remains stationary.

However to engage the second needle 30b, the actuator lever 12 returned to the first actuation lever position and the selection lever 46 is moved to the second selection lever position (e.g., the right) which rotates the cam member 130 in the opposite direction to position the proximal end 115b of the second needle 30b "down" into engagement with the socket 27 of the actuator lever 12 while at the same time positioning the proximal end 115a of the first needle 30a "up" and above the socket 27 of the actuator lever 12. With the proximal end 115b of the second needle 30b so positioned within the socket 27 of the actuator lever 12, pivoting the actuator lever 12 from the first actuation lever position to the second actuation lever position advances the second needle 30b from the first needle position to the second needle position while the first needle 30a that is not engaged with the socket 27 remains stationary.

During a procedure, a surgeon or other user may initially select the first needle 30a using the selection lever 46 as previously described. The surgeon may then position the distal end assembly 24 such that the tissue to be sutured is disposed within the first tissue bite area 35 (illustrated in FIG. 3B). The surgeon may next displace the actuation lever 12 from the first lever position (illustrated in FIG. 1A) to the second lever position (illustrated in FIG. 1B) such that the first needle 30a extends from the first needle position (i.e., a retracted position illustrated in FIGS. 3B and 3C) to the second needle position (i.e., an extended position illustrated in FIGS. 3D and 3E). As the first needle 30a extends to the second needle position, the first needle tip 31a of the first needle 30a engages the first ferrule 33a disposed in the first ferrule recess 73 of the receiving portion 56 such that the first ferrule 33a to be operatively coupled to the first needle tip 31a. As the surgeon releases the actuation lever 12, the actuation lever 12 displaces from the second lever position to the first lever position, thereby displacing the first needle 30a from the second needle position to the first needle position, and in so doing, pulling the first ferrule 33a (and the suture coupled to the first ferrule 33a) through the aperture formed in the tissue disposed within the first tissue bite area 35 by the first needle 30a. The first ferrule 33a may then be disengaged from the first needle tip 31a or may be reloaded into the first ferrule recess 73 (of the second ferrule recess 78) for further suturing.

The surgeon may also select the second needle 30b using the selection lever 46 as previously described. The surgeon may then position the distal end assembly 24 such that the tissue to be sutured is disposed within the second tissue bite area 39 (illustrated in FIG. 3B). The surgeon may next displace the actuation lever 12 from the first lever position (illustrated in FIG. 1A) to the second lever position (illustrated in FIG. 1B) such that the second needle 30b extends from the first needle position (i.e., a retracted position illustrated in FIG. 3D) to the second needle position (i.e., an extended position illustrated in FIG. 3B). As the second needle 30b extends to the second needle position, the second needle tip 31b of the second needle 30b engages the second ferrule 33b disposed in the second ferrule recess 78 of the receiving portion 56 such that the second ferrule 33b to be operatively coupled to the second needle tip 31b. As the surgeon releases the actuation lever 12, the actuation lever 12 displaces from the second lever position to the first lever position, thereby displacing the second needle 30b from the second needle position to the first needle position, and in so doing, pulling the second ferrule 33b (and the suture coupled to the second ferrule 33b) through the aperture formed in the tissue disposed within the second tissue bite area 39 by the second needle 30b. The second ferrule 33b may then be disengaged from the second needle tip 31b or may be reloaded into the second ferrule recess 78 (of the first ferrule recess 73) for further suturing. The tissue sutured with the first needle 30a and the tissue sutured with eh second needle 30b may be adjacent such that the distal end assembly 24 does not need to be repositioned during the procedure.

Various advantages of a surgical equipment holder have been discussed above. Embodiments discussed herein have been described by way of example in this specification. It will be apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and the scope of the claimed invention. The drawings included herein are not necessarily drawn to scale. Additionally, the recited order of processing elements or sequences, or the use of numbers, letters, or other designations therefore, is not intended to limit the claims to any order, except as may be specified in the claims. Accordingly, the invention is limited only by the following claims and equivalents thereto.

What is claimed is:

1. A device comprising:
   a housing portion having a grip portion adapted to be grasped by a hand of a user;
   an actuation lever pivotably coupled to a first portion of the housing portion, the actuation lever configured to be pivoted between a first actuation lever position and a second actuation lever position by the user grasping the grip portion of the housing portion;
   a shaft extending along a shaft axis from a proximal end to a distal end, wherein the proximal end of the shaft is coupled to a second portion of the housing portion;
   a first needle extending along a first needle axis from a proximal end to a distal end, wherein at least a portion of the first needle extends through an interior portion of the shaft, wherein a first needle tip is disposed at the distal end of the first needle, and wherein the proximal end of the first needle is configured to be selectively coupled to a coupling portion of the actuation lever such that when the actuation lever is in the first actuation lever position, the first needle is in a first first needle position, and when the actuation lever is in the second actuation lever position, the first needle is in a second first needle position;
   a second needle extending along a second needle axis from a proximal end to a distal end, wherein at least a portion of the second needle extends through the interior portion of the shaft, wherein a second needle tip is disposed at the distal end of the second needle, and wherein the proximal end of the second needle is configured to be selectively coupled to the coupling portion of the actuation lever such that when the actuation lever is in the first actuation lever position, the second needle is in a first second needle position, and when the actuation lever is in the second actuation lever position, the second needle is in a second second needle position;
   a third needle extending along a third needle axis from a proximal end to a distal end, wherein at least a portion of the third needle extends through the interior portion of the shaft, wherein a third needle tip is disposed at the distal end of the third needle, and wherein the proximal end of the third needle is configured to be selectively coupled to the coupling portion of the actuation lever such that when the actuation lever is in the first actuation lever position, the third needle is in a first third needle position, and when the actuation lever is in the second actuation lever position, the third needle is in a second third needle position;
   a fourth needle extending along a fourth needle axis from a proximal end to a distal end, wherein at least a portion of the fourth needle extends through the interior portion of the shaft, wherein a fourth needle tip is disposed at the distal end of the fourth needle, and wherein the proximal end of the fourth needle is configured to be selectively coupled to the coupling portion of the actuation lever such that when the actuation lever is in the first actuation lever position, the fourth needle is in a first fourth needle position, and when the actuation lever is in the second actuation lever position, the fourth needle is in a second fourth needle position;
   a selection lever coupled to a third portion of the housing portion, the selection lever having a first selection lever position, in which the proximal end of the first needle is coupled with the coupling portion of the actuation lever, a second selection lever position in which the proximal end of the second needle is coupled with the coupling portion of the actuation lever, a third selection lever position in which the proximal end of the third needle is coupled with the coupling portion of the actuation lever, and a fourth selection lever position in which the proximal end of the fourth needle is coupled with the coupling portion of the actuation lever;
   a distal end assembly coupled to the distal end of the shaft, the distal end assembly comprising:
      a base portion extending from a proximal end to a distal end along the shaft axis, the base portion being partially defined by a first base portion, a second base portion, a third base portion and a fourth base portion that each extends from the shaft axis in a direction normal to the shaft axis, and wherein the first base portion, the second base portion, the third base portion, and the fourth base portion cooperate to form an X-shape when viewed along the shaft axis;
      a support portion extending from a proximal end to a distal end along the shaft axis such that the proximal end of the support portion is disposed at the distal end of the base portion; and
      a receiver portion disposed at or adjacent to the distal end of the support portion, the receiver portion partially defined by a first receiver portion, a second receiver portion, a third receiver portion and a fourth receiver portion that each extends from the shaft axis in the direction normal to the shaft axis, and wherein the first receiver portion is aligned with the first base portion, the second receiver portion is aligned with the second base portion, the third receiver portion is aligned with the third base portion, and the fourth receiver portion is aligned with the fourth base portion such that the first receiver portion, the second receiver portion, the third receiver portion, and the fourth receiver portion cooperate to form the X-shape when viewed along the shaft axis, wherein a proximal portion of the first receiver portion, a distal portion of the first base portion, and a first portion of the support portion at least partially define a first tissue bite area, a proximal portion of the second receiver portion, a distal portion of the second base portion, and a second portion of the support portion at least partially define a second tissue bite area, a proximal portion of the third receiver portion, a distal portion of the third base portion, and a third portion of the support portion at least partially define a third tissue bite area, and a proximal portion of the fourth receiver portion, a distal portion of the fourth base portion, and a fourth portion of the support portion at least partially define a fourth tissue bite area, wherein when the selection lever is in the first selection lever position, and when the actuation lever is pivoted from the first actuation lever position to the second actuation lever position, the first needle tip of the first needle extends from a first first needle tip position, in which the first needle tip is proximal to the first tissue bite area, across the first tissue bite area to a second first needle tip position in which the first needle tip is at least partially disposed within a first ferrule recess of the first receiver portion, wherein when the selection lever is in the second selection lever position, and when the actuation lever is pivoted from the first actuation lever position to the second actuation lever position, the second needle tip of the second needle extends from a first second needle tip position, in which the second needle tip is proximal the second tissue bite area, across the second tissue bite area to a second second needle tip position in which the second needle tip is at least partially disposed within a second ferrule recess of the second receiver portion, wherein when the selection lever is in the third selection lever position, and when the actuation lever is pivoted from the first actuation lever position to the second actuation lever position, the third needle tip of the third needle extends from a first third needle tip position, in which the third needle tip is proximal the third tissue bite area, across the third tissue bite area to a second third needle tip position in which the third needle tip is at least partially disposed within a third ferrule recess of the third receiver portion, and wherein when the selection lever is in the fourth selection lever position, and when the actuation lever is pivoted from the first actuation lever position to the second actuation lever position, the fourth needle tip of the fourth needle extends from a first fourth needle tip position, in which the fourth needle tip is proximal the fourth tissue bite area, across the fourth tissue bite area to a second fourth needle tip position in which the fourth needle tip is at least partially disposed within a fourth ferrule recess of the fourth receiver portion.

2. The device of claim 1, wherein the support portion extends along the shaft axis such that the shaft axis longitudinally bisects the support portion.

3. The device of claim 1, wherein the base portion, the support portion, and the receiver portion are a single, unitary part.

* * * * *